(12) United States Patent
Karpeisky et al.

(10) Patent No.: US 10,046,055 B2
(45) Date of Patent: *Aug. 14, 2018

(54) BONE TARGETED THERAPEUTICS AND METHODS OF MAKING AND USING THE SAME

(71) Applicant: MBC Pharma, Inc., Aurora, CO (US)

(72) Inventors: Alexander Karpeisky, Lafayette, CO (US); Shawn Patrick Zinnen, Denver, CO (US)

(73) Assignee: MBC PHARMA, INC., Aurora, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/968,481

(22) Filed: Dec. 14, 2015

(65) Prior Publication Data

US 2016/0095932 A1    Apr. 7, 2016

Related U.S. Application Data

(62) Division of application No. 14/063,951, filed on Oct. 25, 2013, now Pat. No. 9,216,204, which is a division of application No. 12/413,805, filed on Mar. 30, 2009, now Pat. No. 8,586,781.

(51) Int. Cl.

| | | |
|---|---|---|
| *A61K 47/06* | (2006.01) |
| *A61K 31/663* | (2006.01) |
| *C07F 9/38* | (2006.01) |
| *A61K 47/48* | (2006.01) |
| *A61K 31/675* | (2006.01) |
| *A61K 51/04* | (2006.01) |
| *C07F 9/58* | (2006.01) |
| *C07F 9/6512* | (2006.01) |
| *C07F 9/6558* | (2006.01) |
| *C07F 9/6561* | (2006.01) |
| *C07H 19/10* | (2006.01) |
| *C07H 19/207* | (2006.01) |
| *A61K 31/7028* | (2006.01) |
| *A61K 38/14* | (2006.01) |
| *A61K 31/165* | (2006.01) |
| *A61K 31/496* | (2006.01) |
| *A61K 31/546* | (2006.01) |
| *A61K 31/7052* | (2006.01) |

(52) U.S. Cl.
CPC ...... *A61K 47/48084* (2013.01); *A61K 31/165* (2013.01); *A61K 31/496* (2013.01); *A61K 31/546* (2013.01); *A61K 31/663* (2013.01); *A61K 31/675* (2013.01); *A61K 31/7028* (2013.01); *A61K 31/7052* (2013.01); *A61K 38/14* (2013.01); *A61K 47/48023* (2013.01); *A61K 51/0489* (2013.01); *C07F 9/588* (2013.01); *C07F 9/6561* (2013.01); *C07F 9/65121* (2013.01); *C07F 9/65583* (2013.01); *C07F 9/65586* (2013.01); *C07F 9/65616* (2013.01); *C07H 19/10* (2013.01); *C07H 19/207* (2013.01)

(58) Field of Classification Search
CPC .............. A61K 47/48084; A61K 47/06; A61K 31/663; C07F 9/38
See application file for complete search history.

(56) References Cited

U.S. PATENT DOCUMENTS

| | | |
|---|---|---|
| 4,032,625 A | 6/1977 | Subramanian et al. |
| 4,621,077 A | 11/1986 | Rosini |
| 5,130,304 A | 7/1992 | Binderup |
| 5,183,815 A | 2/1993 | Saari et al. |
| 5,358,941 A | 10/1994 | Bechard |
| 5,428,181 A | 6/1995 | Sugioka et al. |
| 5,434,143 A | 7/1995 | Spielvogel et al. |
| 5,488,041 A | 1/1996 | Barbier |
| 5,580,571 A | 12/1996 | Hostetler |
| 5,624,913 A | 4/1997 | Proctor et al. |
| 5,654,286 A | 8/1997 | Hostetler |
| 5,721,219 A | 2/1998 | Ingall |
| 5,760,013 A | 6/1998 | Hwu et al. |
| 5,900,410 A | 5/1999 | Hartmann |
| 6,004,939 A | 12/1999 | Chen et al. |
| 6,121,253 A | 9/2000 | Han |
| 6,140,518 A | 10/2000 | Gallagher |
| 6,214,812 B1 | 4/2001 | Karpeisky et al. |
| 6,605,603 B1 | 8/2003 | Roldan |
| 6,750,340 B2 | 6/2004 | Padioukova et al. |
| 6,896,871 B2 | 5/2005 | Karpeisky et al. |
| 6,929,797 B2 | 8/2005 | Mazess et al. |
| 7,285,658 B2 | 10/2007 | Cook et al. |
| 7,598,246 B2 | 10/2009 | Dixon et al. |
| 8,586,781 B2 | 11/2013 | Karpeisky et al. |
| 2008/0287396 A1 | 11/2008 | Delorme |
| 2009/0239814 A1 | 9/2009 | Manoharan et al. |
| 2014/0051625 A1 | 2/2014 | Karpeisky et al. |
| 2014/0315851 A1 | 2/2014 | Karpeisky et al. |
| 2014/0329768 A1 | 11/2014 | Karpeisky et al. |

FOREIGN PATENT DOCUMENTS

| | | |
|---|---|---|
| CA | 2443856 | 6/2012 |
| DE | 19 18 282 | 10/1969 |
| EP | 0 100 718 | 2/1984 |
| EP | 0 512 844 | 11/1992 |
| EP | 2 260 852 | 1/2011 |

(Continued)

OTHER PUBLICATIONS

Boyle et al, 2005, Nucleosides, Nucleotides and Nucleic Acids, vol. 24, p. 1651-1664.*

(Continued)

*Primary Examiner* — Rebecca L Anderson
*Assistant Examiner* — Karen Cheng
(74) *Attorney, Agent, or Firm* — FisherBroyles, LLP; Cara L. Crowley-Weber

(57) ABSTRACT

The present invention provides novel bisphosphonate conjugates, pharmaceutical compositions comprising bisphosphonate conjugates and methods of using such analogs in the treatment of bone cancer, bone-related diseases, bone infection, bone inflammation, and diseases of the soft tissues surrounding bones.

11 Claims, 6 Drawing Sheets

(56) References Cited

FOREIGN PATENT DOCUMENTS

| WO | 1988/000829 | 2/1988 |
|----|-------------|--------|
| WO | 1991/010646 | 7/1991 |
| WO | 1993/07157  | 4/1993 |
| WO | 1996/040156 | 12/1996 |
| WO | 1997/002279 | 1/1997 |
| WO | 1998/035704 | 8/1998 |
| WO | 2002/083150 | 10/2002 |
| WO | 2012/158811 | 11/2012 |
| WO | 2013/019874 | 2/2013 |

OTHER PUBLICATIONS

Buxton et al. (1998) Abstracts of the Interscience Conference on Antimicrobial Agents and Chemotherapy 38:29 "Ciprofloxacin Conjugated to Bisphosphonate: Characterization fo Bone Affinity In Vitro" XP008043693.
Buxton et al. (2001) FASEB Journal 15(4):A587 "Novel Local Drug Delivery of Antibiotic-Bisphosphonate: Binding and Antibacterial Effects" XP008043697.
European Search Report from EP 10 18 3006 dated Dec. 13, 2010.
Fleisch (1998) Endocrine Reviews 19(1):80-100 "Bisphosphonates: Mechanisms of Action".
Fujisaki et al. (1995) Proceedings of the International Symposium on Controlled Release of Bioactive Materials, 22:562-3 "Osteotropic Drug Delivery System(ODDS) Based on Bisphosphonic Prodrug".
Gough et al. (1973) Journal of Medicinal Chemistry; 16(10):1188-1190 "Three New Adenosine Triphosphate Analogs, Synthesis and Effects on Isolated Gut".
Herczegh et al. (2002) J. Med. Chem. 45:2338-2341 "Osteoadsorptive bisphosphonate derivatives of fluoroquinolone antibacterials".
Hershey and Monro (1966) J. Mol. Biol. 18:68-76 "A Competitive Inhibitor of the GTP Reaction in Protein Synthesis".
Hosain et al. (1996) The Journal of Nuclear Medicine 37(1):105-107 "Targeted Delivery of Antineoplastic Agent to Bone: Biodistribution Studies of Technetium-99m-Labeled Gem-Bisphosphonate Conjugate of Methotrexate".
Houghton et al. (2008) J. Med. Chem. 51(21): 6955-6969 "Linking bisphosphonates to the free amino groups in fluoroquinolones: preparation of osteotropic prodrugs for the prevention of osteomyelitis".
International Search Report & Written Opinion with respect to PCT/US2012/049181 dated Dec. 19, 2012.
Klein (1998) Journal of Cellular Biochemistry 68:186-194 "Structurally Different Bisphosphonates Exert Opposing Effects on Alkaline Phosphatase and Mineralization in Marrow Osteoprogenitors".
Lincosamides (2013) thefreedictionary.com Website: http://medical-dictionary.thefreedictionary.com/p/lincosamides, retrieved Mar. 20, 2013.
Murud et al. (1999) Nuclear Medicine and Biology 26(7):791-794 "Influence of Pretreatment with 3-Amino-1-Hydroxypropylidene-1,1-Bisphosphonate (APB) on Organ Uptake of 211At and 125I-Labeled Amidobisphosphonates in Mice".

Nancollas et al. (2006) Bone 38:617-627 "Novel Insights into Actions of Bisphosphonates on Bone: Differences in Interactions with Hydroxyapatite".
Ono et al. (1989) Molecular Pharmacology 35:578-583"Differential Inhibitory Effects of Several Pyrimidine 2', 3'-Dideoxynucleoside 5'-Triphosphates on the Activities of Reverse Transcriptase and Various Cellular DNA Polymerases".
Ora et al. (2008) Journal Organic Chemistry 73:4123-4130 "Bisphosphonate Derivatives of Nucleoside Antimetabolites: Hydrolytic Stability and Hydroxyapatite Adsorption of 5'-β,γ-Methylene and 5'β,γ-(1-Hydroxyethylidene) Triphosphates of 5-Fluorouridine and ara-Cytidine".
Padyukova et al. (1999) Nucleosides & Nucleotides 18(4&5):1013-1014 "Synthesis and Properties of Novel NTP Derivatives".
Reddy et al. (2008) ChemMedChem 3: 1863-1868 "Bisphosphonated benzoxazinorifamycin prodrugs for the prevention and treatment of osteomyelitis".
Reinholz et al. (2002) Breast Cancer Research and Treatment 71:257-268 "Distinct mechanisms of bisphosphonate action between osteoblasts and breast cancer cells: identity of a potent new bisphosphonate analogue".
Renis (1973) Antimicrobial Agents and Chemotherapy 4(4):439-444 "Antiviral Activity of Cytarabine in Herpesvirus-Infected Rats".
Rocha et al. (2000) "Pyridoxine (vitamin B6) stimulates osteoblastic differentiation in vitro—Presentation No. SA213" Journal of Bone and Mineral Research XP-002609426.
Rogers et al. (1995) Molecular Pharmacology 47:398-402 "Structure-Activity Relationships of New Heterocycle-Containing Bisphosphonates as Inhibitors of Bone Resorption and as Inhibitors of Growth of Dictyostelium discoideum Amoebae".
Shirokova et al. (1999) Nucleosides and Nucleosides 18(4 &5):1027-1028"Modified Nucleoside 5'-Triphosphonates as a New Type of Antiviral Agents".
Shtil et al. (2000) Proceedings of the American Association for Cancer Research Annual Meeting 41:398 "Novel Bisphosphonate-Based Compounds for Circumventing Drug Resistance in the Bone-Targeting Human Tumor" XP-002319674.
Sofia, M.J. (2011) "Nucleotide Prodrugs for HCV Therapy," Antiviral Chemistry & Chemotherapy, 22:23-49.
Tagaya et al. (1985) "A New Affinity Labeling Reagent for the Active Site of Glycogen Synthase," Journal of Biological Chemistry, 260(11):6670-6676.
Tanaka et al. (2008) Bioorganic and Medicinal Chemistry 16: 9217-9229 "Bisphosphonated fluoroquinolone esters as osteotropic prodrugs for the prevention of osteomyelitis".
Wermuth (1996) Academic Press, 203-237 (book chapter) "Molecular Variations Based on Isoteric Replacements".
Zhang and McCormick (1991) Proc. Natl. Acad. Sci. 88:10407-10410 "Uptake of N-(4'-Pyridoxyl)Amines and Release of Amines by Renal Cells: a Model for Transporter-Enhanced Delivery of Bioactive Compounds".

\* cited by examiner

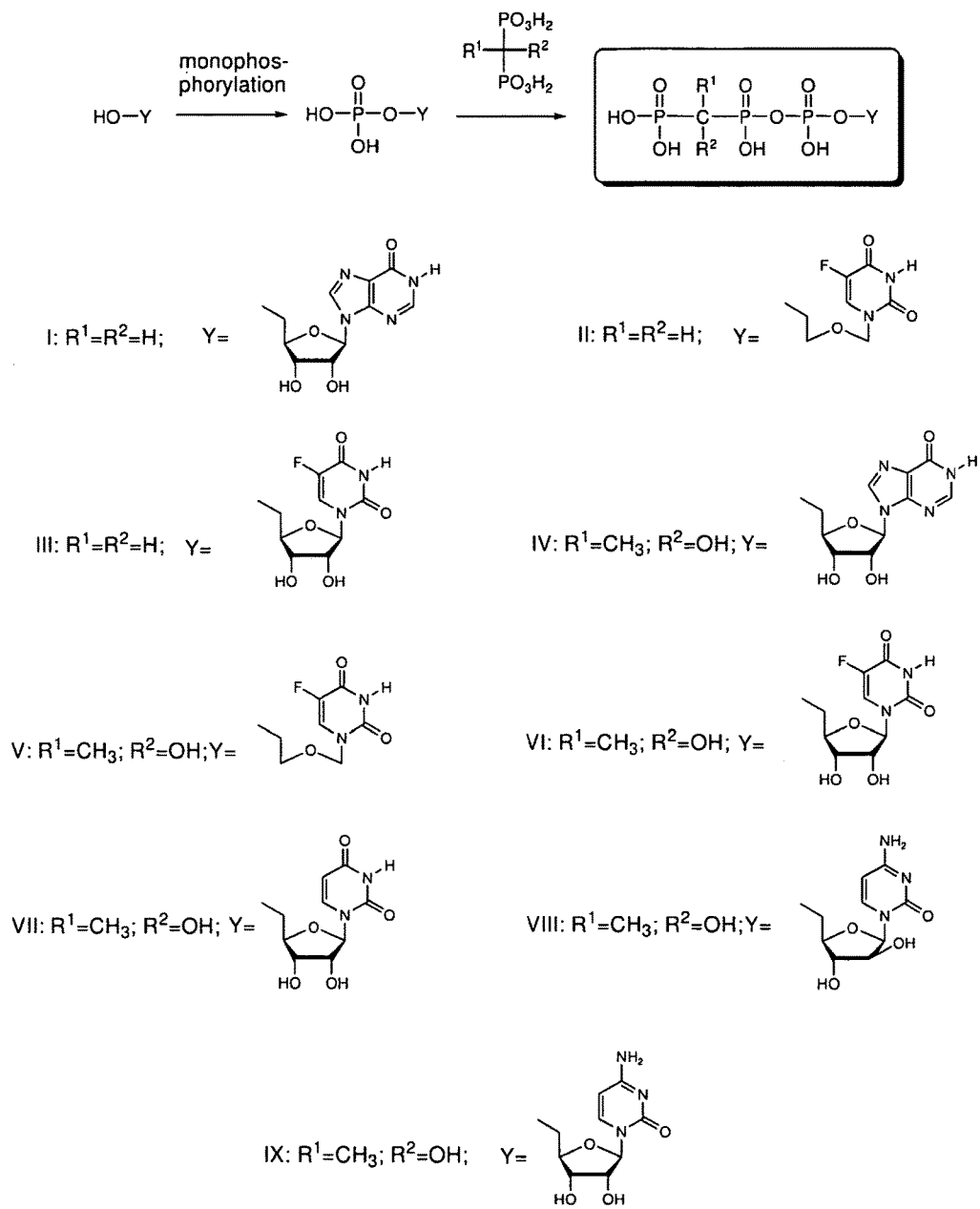
Fig. 1 SYNTHESIS OF NUCLEOSIDE-BISPHOSPHONATE CONJUGATES

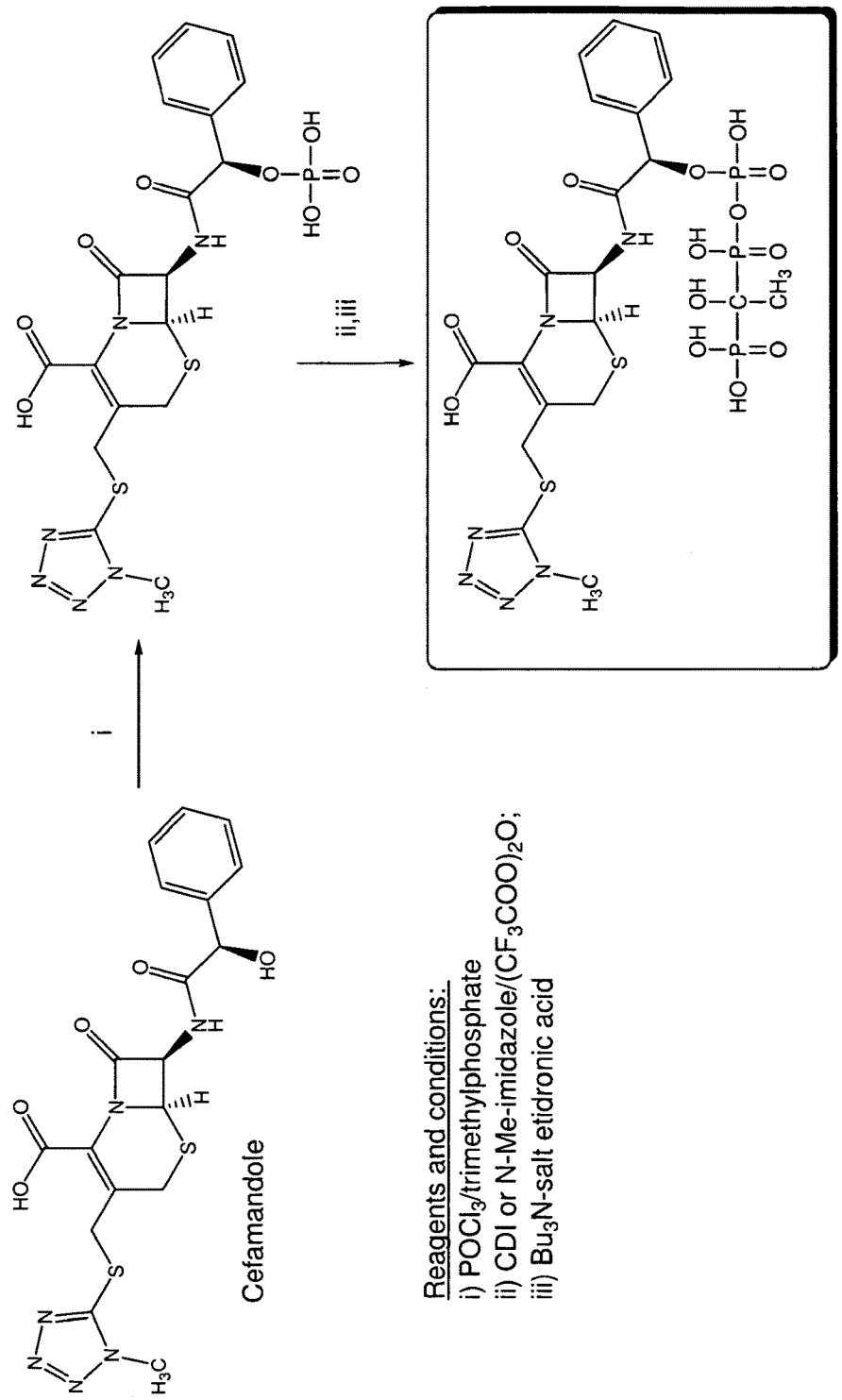
Fig. 2 SYNTHESIS OF CEFAMANDOLE-ETIDRONATE CONJUGATE
Reagents and conditions:
i) POCl$_3$/trimethylphosphate
ii) CDI or N-Me-imidazole/(CF$_3$COO)$_2$O;
iii) Bu$_3$N-salt etidronic acid

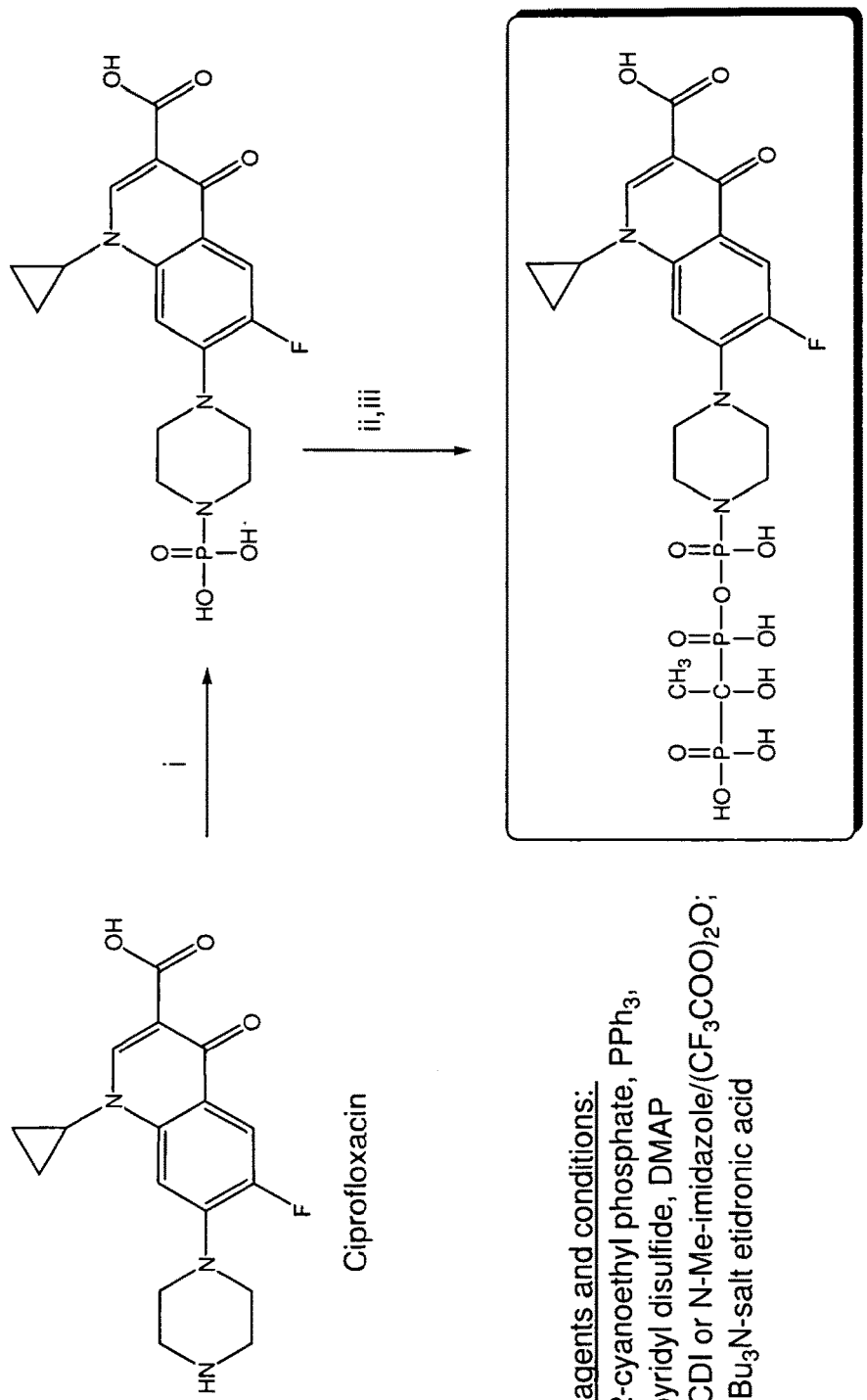
Fig. 3 SYNTHESIS OF CIPROFLOXACIN-ETIDRONATE CONJUGATE
Reagents and conditions:
i) 2-cyanoethyl phosphate, PPh₃, dipyridyl disulfide, DMAP
ii) CDI or N-Me-imidazole/(CF₃COO)₂O;
iii) Bu₃N-salt etidronic acid Fig. 4 SYNTHESIS OF TELAVANCIN-ETIDRONATE CONJUGATE
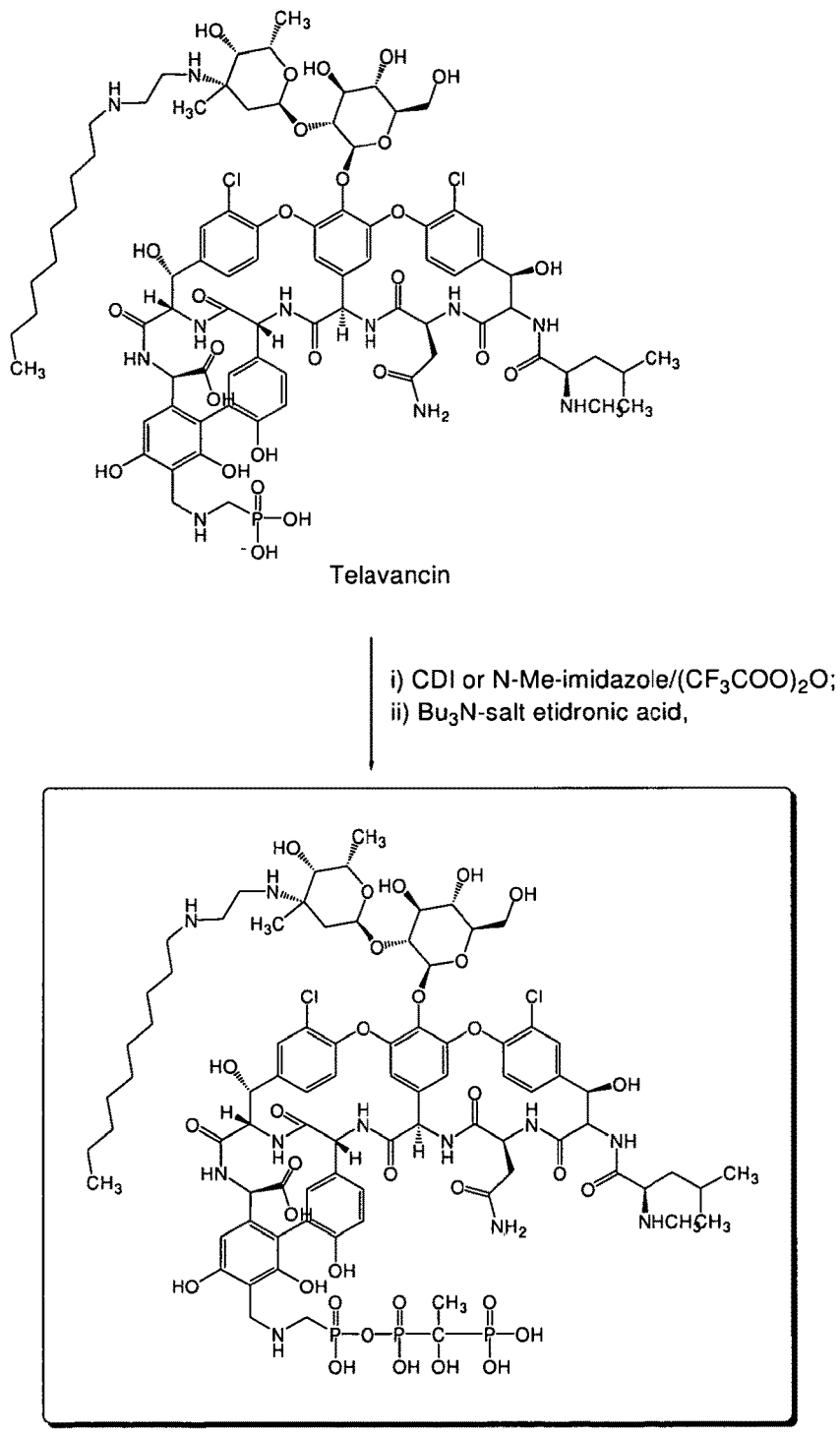

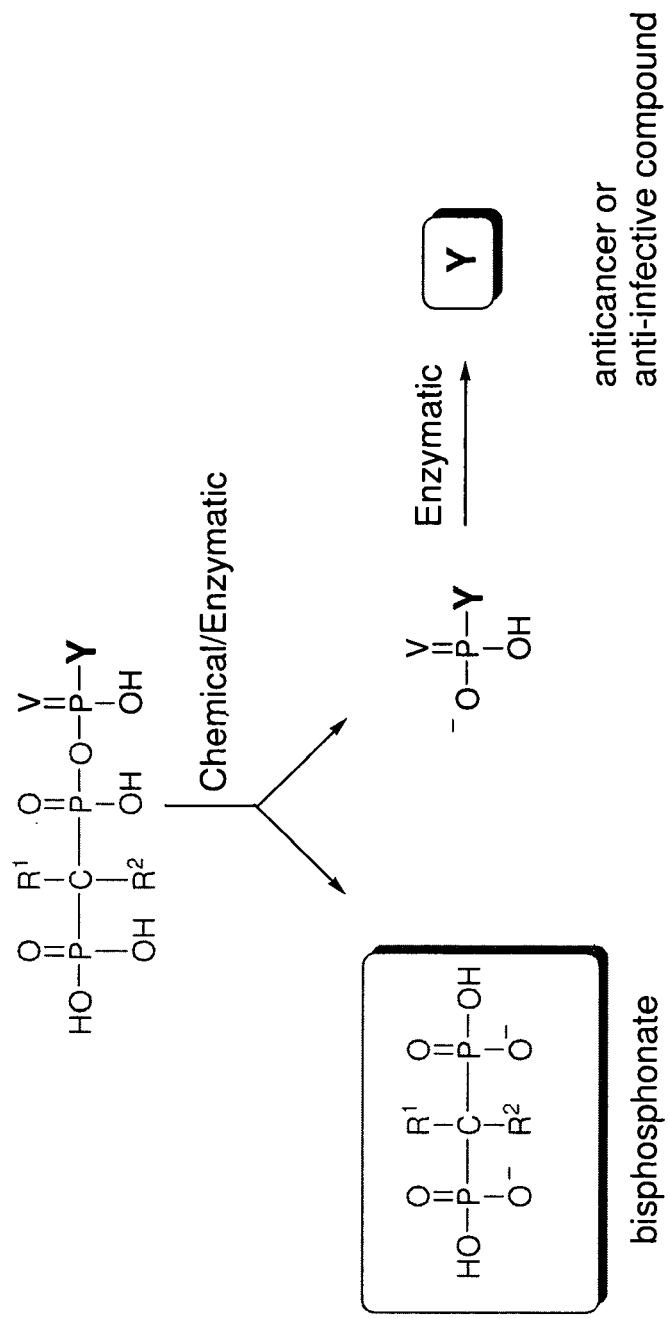
Fig. 5 DEGRADATION OF CONJUGATES ON BONE

Fig. 6 FEMUR ASSOCIATED RADIOACTIVITY
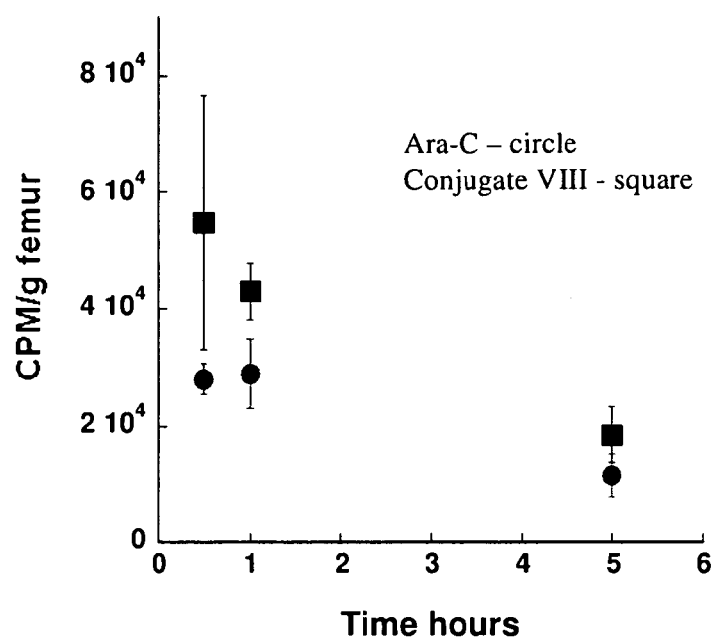

BONE TARGETED THERAPEUTICS AND METHODS OF MAKING AND USING THE SAME

CROSS-REFERENCE TO RELATED APPLICATIONS

This application is a divisional of U.S. patent application Ser. No. 14/063,951, filed Oct. 25, 2013, which is a divisional application of U.S. patent application Ser. No. 12/413,805, filed Mar. 30, 2009, now U.S. Pat. No. 8,586,781. The disclosures of these applications are incorporated herein by this reference.

FIELD

The present invention is directed to bisphosphonate compounds, and in particular, bisphosphonate conjugates that are useful in the treatment of soft tissues surrounding bone and bone-related diseases, such as bone cancer and osteoporosis.

BACKGROUND

Bone degeneration diseases, including Paget's Disease and osteoporosis have proven difficult to treat because the mechanisms involved in the development and progression of these diseases are not well understood. Bisphosphonates are synthetic analogs of pyrophosphates characterized by a phosphorus-carbon-phosphorus backbone that renders them resistant to hydrolysis and are known to be useful in the treatment of these degenerative bone disorders. The chemical properties of the bisphosphonates vary based on different substitutions at the carbon atom of the phosphorus-carbon-phosphorus backbone.

Bisphosphonates bind strongly to hydroxyapatite on the bone surface and act to reduce and inhibit the activity of osteoclasts; cells functioning in the absorption and removal of osseous tissue. The anti-resorptive effect of bisphosphonates is also mediated through effects on osteoblasts; cells that function in the production of bone. Thus, biophosphonates are used clinically to inhibit bone resorption in disease states such as Paget's disease, osteoporosis, metastatic bone diseases, and malignant and nonmalignant hypercalcemia. Bisphosphonates are also used to mediate anti-cancer effects by modifying the bone surface, altering the bone microenvironment, inhibiting specific enzymatic pathways and inducing apoptosis in osteoclast and tumor cells.

Bisphosphonates that are currently used therapeutically include alendronate, clodronate, etidronate, pamidronate, tiludronate, ibandronate, zoledronate, olpadronate, residronate and neridronate. Additionally, bone scanning agents based on the use of bisphosphonic acid compounds have been used in the past to produce high definition bone scans (see e.g., U.S. Pat. No. 4,810,486 to Kelly et. al). Bisphosphonate derivatives have been used as therapeutic agents for bone diseases such as osteoporosis, rheumatoid arthritis, and osteoarthritis (see e.g., U.S. Pat. No. 5,428,181 to Sugioka et. al). In the past, however, bisphosphonate therapies have frequently been accompanied by severe side effects such as retardation of bone development and somatic growth.

Therefore, a need exists for novel bisphosphonate compounds that act as delivery vehicles to target and deliver therapeutic agents to bone and the surrounding soft tissue, allowing selective treatment of these tissues while eliminating or minimizing the severe side effects previously seen with bisphosphonate therapies.

SUMMARY

Provided herein are bone-seeking conjugates containing anticancer or anti-infective compounds or derivatives thereof linked to bisphosphonates. When linked to a moiety having antineoplastic or anti-infective properties, bisphosphonates act as vehicles for the targeted delivery of these therapeutic entities to bone. The chemical bond(s) connecting the bisphosphonate and the drug is/are stable enough to survive in the bloodstream and yet is/are cleaved to liberate the drug when the conjugate binds to bone.

Because these conjugates are capable of releasing anti-infective and cytotoxic components upon binding with bone tissue, they are useful in the treatment and prevention of bone cancer, bone infections, bone inflammation and disorders in soft tissues surrounding bone. For example, in the case of osteomyelitis, certain therapeutic anti-infectives can be coupled to the bisphosphonate carrier molecule for delivery of high concentrations of anti-infective therapy to various sites of bone infection. Examples of useful anti-infectives that can be coupled with the bisphosphonates of the present invention include fluoroquinolones; lincosamides; oxazolidinones, aminoglycoside antibiotics; cephalosporins, lipoglycopeptides. Examples of useful anticancer derivatives that can be conjugated with the bisphosphonates of the present invention include 5-fluorouracil, cytarabine, cisplatin, doxorubicin, epirubicin, streptozocin.

One embodiment of the present invention provides novel bisphosphonate conjugates that are capable of delivering anti-infective and/or anti-neoplastic (cytotoxic) residues to the bone and surrounding tissues. Such conjugates will release their therapeutic component upon binding to the bone tissue and thus are useful in the treatment and prevention of bone primary tumors, metastases of non-bone tumors to bones and infections of bone and surrounding soft tissue.

The conjugates of the present invention comprise anhydrides formed between a substituted bisphosphonic acid and phosphate, thiophosphate or phosphoramidate derivatives of anticancer or anti-infective compounds. The labile phosphoanhydride bond in such analogs provides release of the therapeutic compound upon binding with the bone or surrounding tissues.

Another embodiment of the present invention provides substituted bisphosphonic acids linked to therapeutic entities that are effective in treating or modulating cancers or infections of bone and bone-surrounding tissues such as amino acids, nucleic acids, protein toxins, protein and/or peptide growth factors and hormones that promote bone growth and bone marrow proliferation.

Another aspect of the present invention provides bisphosphonate conjugates that offer a delivery vehicle with which to deliver and concentrate drugs and proteins to normal and abnormal bone tissue and soft tissue surrounding bones. These abnormalities are generally referred to as bony lesions. As used herein, bony lesions include, but are not limited to, bone cancer, osteomyelitis, soft tissue infections surrounding bone, bone marrow abnormalities, and bone diseases such as Paget's disease.

The present invention thus provides novel bone targeted therapeutics, pharmaceutical compositions comprising said bone-targeted therapeutics and methods of using such analogs in the treatment of bone cancer, bone-related diseases and diseases of the soft tissues surrounding bones.

BRIEF DESCRIPTION OF THE DRAWINGS

FIG. 1 is the synthetic scheme for the preparation of nucleoside-5'-triphosphate analogs.

FIG. 2 demonstrates the synthesis of cefamandole-etidronate conjugate.

FIG. 3 demonstrates the synthesis of ciprofloxacin-etidronate conjugate.

FIG. 4 demonstrates the synthesis of telavancin-etidronate conjugate.

FIG. 5 shows degradation of the bisphosphonate conjugates on bone.

FIG. 6 shows distribution of the conjugate on bone.

DETAILED DESCRIPTION

The present invention relates to novel bone-targeted therapeutics that are capable of delivering therapeutic compounds such as anti-infective and/or anti-neoplastic (cytotoxic) compounds or peptide or protein compounds, having growth stimulating properties, to bone and soft tissues surrounding bone. The conjugates release the therapeutic components upon binding to the bone tissue and are therefore useful in the treatment and prevention of primary bone tumors, metastases to bone tissues, bone inflammation, bone infections (and inflammation caused by bone infection) and disorders of the growth of bone and bone marrow. It is understood that compounds of the invention may be covalently linked together either via linker or directly.

Bisphosphonates are synthetic compounds containing two phosphonate groups bound to a central (geminal) carbon (the P—C—P backbone) that are used to prevent bone resorption in a number of metabolic and tumor-induced bone diseases including multiple myeloma. Bisphosphonate treatment is associated with an increase in patient survival, indicating that these compounds have a direct effect on the tumor cells.

Bisphosphonates may contain two additional chains bound to the central geminal carbon. The presence of these two side chains allows numerous substitutions to the bisphosphonate backbone and therefore the development of a variety of analogs with different pharmacological properties. The activity varies greatly from compound to compound, the newest bisphosphonates being 5,000 to 10,000 times more active than etidronate, the first bisphosphonate described. The mechanism of action of bisphosphonates includes a direct effect exerted on osteoclast activity, direct and indirect effects on osteoclast recruitment mediated by cells of the osteoblastic lineage and involving the production of an inhibitor of osteoclastic recruitment and a shortening of osteoclast survival by apoptosis.

High doses of bisphosphonates can also inhibit mineralization through a physicochemical inhibition of crystal growth. One substituent on the geminal carbon together with the P—C—P backbone are primarily responsible for binding to bone mineral and for the physicochemical actions of the bisphosphonates. These interactions are optimized by the presence of a hydroxyl group as at least one substituent on the geminal carbon. The remaining substituent on the geminal carbon is responsible for the anti-resorptive action of the bisphosphonates and small modifications or conformational restrictions at this part of the molecule result in marked differences in anti-resorptive potency. The presence of nitrogen functionality in an alkyl chain or in a ring structure in one of the substituents on the geminal carbon greatly enhances the anti-resorptive potency and specificity of bisphosphonates for bone resorption and most of the newer potent bisphosphonates contain nitrogen atom in their structure.

The biological effects of bisphosphonates in calcium-related disorders are attributed to the incorporation of the bisphosphonates into bone, enabling direct interaction with osteoclasts and/or osteoblasts. The high accumulation of bisphosphonates in bone, due to their high affinity for hydroxyapatite, is essential for mediating both the in vitro and in vivo activity. Nitrogen-containing bisphosphonates are known to act by binding to a specific intracellular target at a site complementary in structure to the bisphosphonate side chain.

Recent evidence suggests that the whole bisphosphonate molecule is essential for anti-resorptive action. Thus, although the basic structural requirements for bisphosphonate actions have been defined, precise structure-activity relationships for the bisphosphonate side chains indicate that at least the newer generations of nitrogen-containing bisphosphonates act by binding to a specific target at a site that is complementary in structure to the bisphosphonate side chain.

The bisphosphonate conjugates of the present invention have the chemical structure:

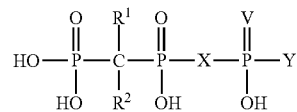

wherein,

X is O,

V is O or S

Y is an anti-infective or anticancer compound, having in its structure free functional group, used for conjugation with the linker. Examples of such groups include but are not limited to OH, $NH_2$, NH, N-alkyl.

$R^1$ is selected from the group consisting of OH, SH, $NH_2$, OZ, SZ, NZ, halogen, H and;

$R^2$ is selected from the group consisting of H, Z, and halogen; and

Z is selected from the group consisting of alkyl, cycloalkyl, aryl, heteroaryl, and $NH_2$.

Additionally, compounds of present invention have the following structure:

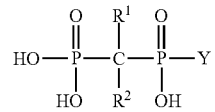

wherein,

Y is an anti-infective or anticancer compound, having in its structure free functional group, used for conjugation with the linker. Examples of such groups include but are not limited to $PO_3H_2$;

$R^1$ is selected from the group consisting of OH, SH, $NH_2$, OZ, SZ, NZ, halogen, and H;

$R^2$ is selected from the group consisting of H, Z, and halogen; and

Z is selected from the group consisting of alkyl, cycloalkyl, aryl, heteroaryl, and $NH_2$.

Additionally, compounds of present invention may contain one or more bisphosphonate residues and have the following structure:

$Y(L-A)_n$ n=1-10, for example, n=1-3

A is a bisphosphonate residue having structure

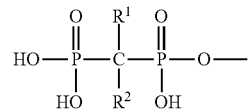

Where $R^1$ is selected from the group consisting of OH, SH, $NH_2$, OZ, SZ, NZ, halogen, and H;

$R^2$ is selected from the group consisting of H, Z, and halogen;

Z is selected from the group consisting of alkyl, cycloalkyl, aryl, heteroaryl, and $NH_2$;

L is a linker, having structure

Where V is O or S; and

Y is a residue of anti-infective or anticancer compound, having in its structure free functional group, used for conjugation with the linker. Examples of such groups include but are not limited to OH, $NH_2$, NH, and N-alkyl.

As used herein, an "alkyl" group refers to a saturated aliphatic hydrocarbon, including straight-chain and branched-chain alkyl groups. Preferably, the alkyl group has 1 to 12 carbons. More preferably it is a lower alkyl having from 1 to 7 carbons, and more preferably 1 to 4 carbons. The alkyl group may be substituted or unsubstituted. When substituted, the substituent group(s) may include hydroxy, cyano, alkoxy, $NO_2$ or $N(Alkyl)_2$, NHAlkyl, amino, or SH.

As used herein, a "cycloalkyl" group refers to a cyclic alkyl group having from three to ten, and preferably five or six carbon atoms forming the alkyl ring.

As used herein, an "aryl" group refers to an aromatic group which has at least one ring having a conjugated pi electron system and includes carbocyclic aryl, heterocyclic aryl and biaryl groups; all of which may be optionally substituted. Substituent(s) on these groups may include halogen, trihalomethyl, hydroxyl, SH, cyano, alkoxy, alkyl, alkenyl, alkynyl, and amino groups.

As used herein, "heteroaryl" refers to an aromatic ring having from 1 to 3 heteroatoms in the aromatic ring with the remainder of the atoms in the ring being carbon atoms. Suitable heteroatoms include oxygen, sulfur, and nitrogen, and exemplary heteraryls include furanyl, thienyl, pyridyl, pyrrolyl, pyrrolo, pyrimidyl, pyrazinyl and imidazolyl. These heteroaryl rings may also be substituted. Substituents on these heteroaryl groups may include halogen, trihalomethyl, hydroxyl, SH, cyano, alkoxy, alkyl, alkenyl, alkynyl, and amino groups.

As used herein, "anti-infective compound" refers to any compound having antibacterial, antibiotic, antifungal, antiprotozoan and antiviral activity.

As used herein, "halogen" refers to Cl, F, or Br atom.

The bisphosphonate conjugates of the present invention contain both an osteotropic moiety and a therapeutic moiety that is released from the osteotropic moiety upon binding of the conjugates to bone tissue. The covalent bond(s) connecting the bisphosphonate moiety and the therapeutic component are stable enough to survive in the bloodstream but are cleaved to liberate the drug when the conjugate binds to bone tissue, releasing the therapeutic component to the bone or to soft tissue surrounding the bone.

These bisphosphonate conjugates comprise conjugates formed between a substituted bisphosphonate and a substituted phosphoric, thiophosphoric or amidophosphoric acid. Thus, these conjugates are analogs of triphosphates. It is the labile phosphoanhydride bonds in these analogs that release the conjugated therapeutic compounds upon binding with the bone. In this way, the bisphosphonate conjugates of the present invention can be used to target covalently bound therapeutic compounds to bone and soft tissue surrounding bone.

One embodiment of the present invention includes anticancer drugs that are coupled to bisphosphonate or derivatives of bisphosphonate substituted at the geminal carbon. The anti-cancer drugs may include, but are not limited to, nucleosides and/or acyclo-nucleosides in which the sugar or nucleic base is modified or unmodified (natural), antisense and catalytic oligonucleotides, amino acids, peptides, polypeptides or proteins having cytostatic or antineoplastic properties. The bisphosphonate may also be conjugated to combinations of one or more of these anti-cancer compounds. Exemplary anticancer compounds for conjugation to the bisphosphonate moiety include, but are not limited to, cytarabine, cisplatin, doxorubicin, epirubucin, streptozocin. Additionally, the bisphosphonate or bisphosphonate derivatives may be conjugated to nucleosides or nucleoside-like compounds having cytostatic or neoplastic activity. Exemplary nucleoside or nucleoside-like compounds that can be conjugated to the bisphosphonate compounds of the present invention include compounds having the structure:

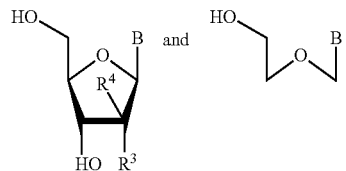

wherein $R^3$ and $R^4$ are independently H, OH or F and B is a natural or modified nucleic base or derivative thereof. Exemplary modified nucleic bases include compounds having the structure:

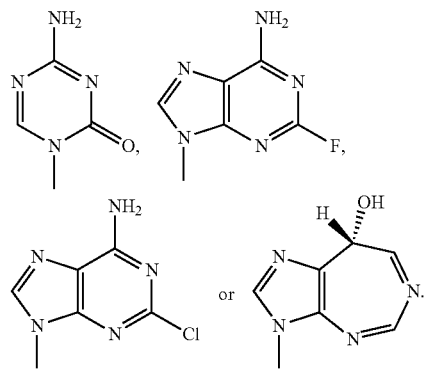

These nucleoside or nucleoside-like compounds can be linked to the bisphosphonate or bisphosphonate derivatives through a linker group. Exemplary linking moieties include phosphate or thiophosphate groups. These bisphosphonate conjugates are useful in the treatment of primary bone tumors, bone metastases (i.e. metastases to bone tissues from malignant tissue elsewhere in the body), bone inflammation, bone infections and disorders of the growth of bone and bone marrow. Thus, the present invention includes methods of treating a mammal in need of anti-cancer therapy with compounds of the present invention having an anti-cancer compound coupled to a bisphosphonate in a therapeutically effective amount sufficient to impart a chemotherapeutic response in the mammal.

Another embodiment of the present invention includes a bisphosphonate or derivatives of bisphosphonate substituted at the geminal carbon coupled to a compound having anti-infective activity. These conjugates have been found to be particularly useful in the treatment of infections or inflammation of the bone tissue or of soft tissues surrounding bone. In this embodiment, therapeutic anti-infective compounds can be coupled directly (if an anti-infective compound has a free phosphate or phosphonate residue in its structure such as telavancin) to the bisphosphonate carrier molecule or via phosphate or thiophosphate group linker, for delivery of high concentrations of anti-infective compound to the sites of bone or soft tissue infection or inflammation. The covalent bond(s) connecting the bisphosphonate moiety and the anti-infective moiety are cleaved to liberate drug when the conjugate binds to bone tissue, releasing the anti-infective compound to the bone or to soft tissue surrounding the bone (FIG. 5).

Examples of anti-infective compounds which can be conjugated to the bisphosphonate carriers include, but are not limited to, fluoroquinolones such as ciprofloxacin; lincosamides such as clindamycin; oxazolidinones such as eperezolid; aminoglycoside antibiotics such as gentamycin; cephalosporin antibiotics such as cephamandole; glycopeptides such as vancomycin or telavancin; fusidic acid and chloramphenicol.

An exemplary clindamycin residue is shown below:

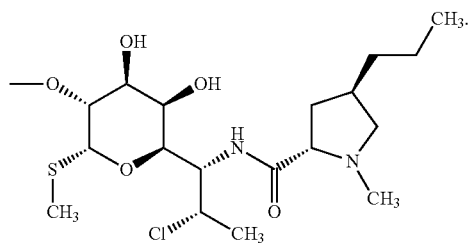 [SMILES: CCC[C@@H]1C[C@@H](C(=O)N[C@@H]([C@H]2O[C@H](SC)[C@H](OC)[C@@H](O)[C@H]2O)[C@H](C)Cl)N(C)C1]

An exemplary cefamandole residue is shown below:

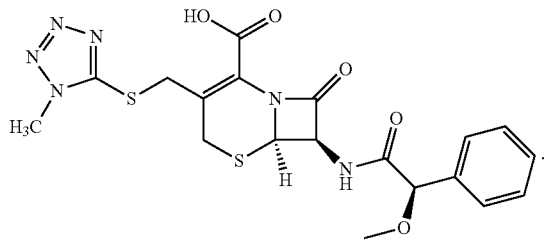 [SMILES: CO[C@@H](C(=O)N[C@@H]1C(=O)N2C(C(=O)O)=C(CSc3nnnn3C)CS[C@H]12)c1ccccc1]

An exemplary eperezolid residue is shown below:

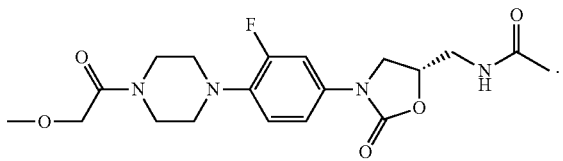 [SMILES: COCC(=O)N1CCN(c2ccc(N3C[C@H](CNC(C)=O)OC3=O)cc2F)CC1]

Exemplary chloramphenicol residues include:

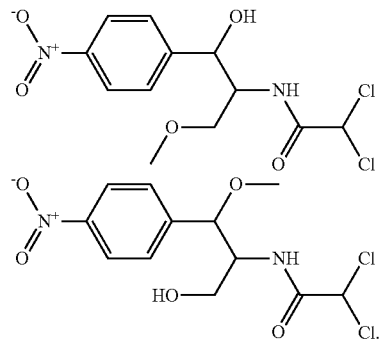

An exemplary ciprofloxacin residue is shown below:

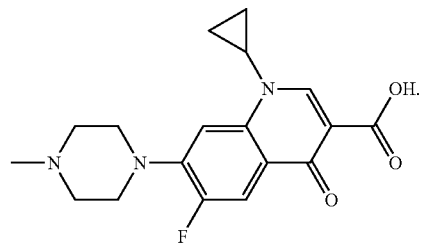 [SMILES: CN1CCN(c2cc3c(cc2F)c(=O)c(C(=O)O)cn3C2CC2)CC1]

An exemplary vancomycin residue is shown below:

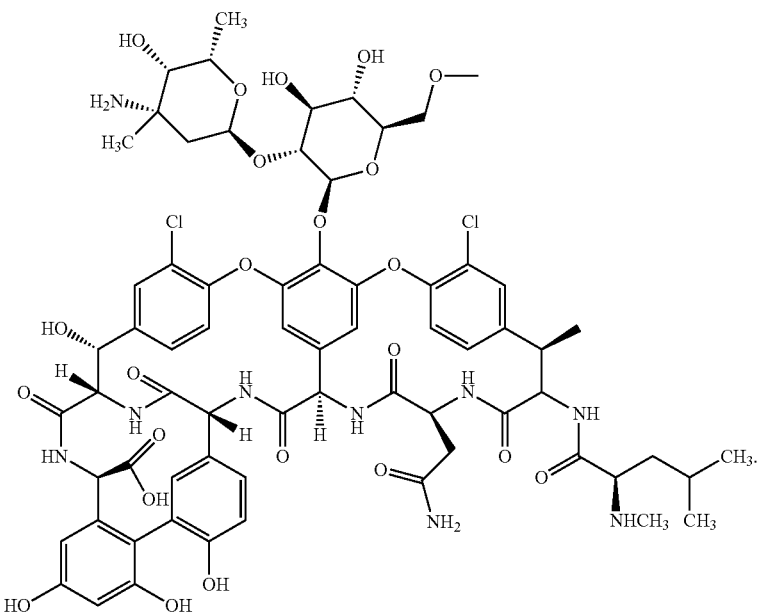 [SMILES: CN[C@H](CC(C)C)C(=O)NC1C(=O)N[C@@H](CC(N)=O)C(=O)N[C@H]2C(=O)N[C@H]3C(=O)N[C@H](C(=O)N[C@@H](C(=O)O)c4cc(O)cc(O)c4-c4cc3ccc4O)[C@H](O)c3ccc(c(Cl)c3)Oc3cc2cc(c3O[C@@H]2O[C@H](COC)[C@@H](O)[C@H](O)[C@H]2O[C@H]2C[C@](C)(N)[C@H](O)[C@H](C)O2)Oc2ccc(cc2Cl)[C@H]1C]

An exemplary telavancin residue is shown below:

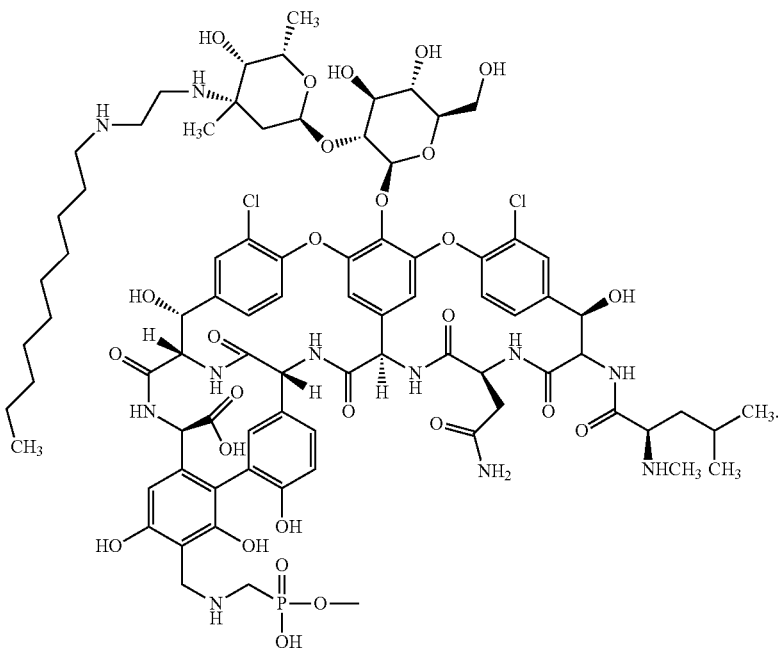 [SMILES: CCCCCCCCCCNCCN[C@@]1(C)C[C@H](O[C@H]2[C@H](Oc3c4cc5cc3Oc3ccc(cc3Cl)[C@@H](O)[C@@H]3NC(=O)[C@H](NC(=O)[C@@H]5NC(=O)[C@H](CC(N)=O)NC(=O)C(NC(=O)[C@@H](CC(C)C)NC)[C@H](O)c5ccc(c(Cl)c5)O4)c4ccc(O)c(c4)-c4c(cc(O)c(CNCP(=O)(O)OC)c4O)[C@H](C(=O)O)NC3=O)O[C@H](CO)[C@@H](O)[C@@H]2O)O[C@@H](C)[C@H]1O]

Examples of bisphosphonate carriers include but are not limited to etidronate, clodronate, pamidronate, alendronate, risedronate, zoledronate, medronic acid, aminomethylene bisphosphonic acid.

The present invention also includes methods of treating a mammal in need of anti-infective or anti-inflammatory or anticancer therapy with compounds of the present invention having an anti-infective or anti-inflammatory or anticancer compound coupled to a bisphosphonate, in a therapeutically effective amount to impart anti-infective or anti-inflammatory or anticancer responses in the mammal. Illustratively, an anti-infective compound coupled to a bisphosphonate is useful for treating or preventing bone infection and/or bone inflammation.

Another embodiment of the present invention is a bisphosphonate or derivatives of bisphosphonate substituted at the geminal carbon moiety conjugated to a protein or peptide growth factor or hormone that promotes bone growth and/or bone marrow proliferation. These conjugates are useful in the treatment of diseases or abnormalities of bone formation, bone resorption or bone growth. Thus, the present invention includes methods of treating a mammal in need of therapy to slow, stabilize or increase bone growth with compounds of the present invention having bone growth regulating proteins coupled to a bisphosphonate in a therapeutically effective amount to impart the desired negative or positive bone growth response in the mammal.

Compounds and conjugates provided herein can offer a number of novel benefits to the task of delivering therapeutics to the bone. First the conjugation to bisphosphonate alters the pharmacokinetics such the majority of drug is either bound to bone or cleared renally; this is due to the highly charged nature of the bisphosphonate and the inability of cells to uptake such compounds in significant amounts. A further advantage is the reduced systemic exposure and thus the systemic toxicity associated with otherwise effective compounds. This may enable the use of higher concentrations of a drug than would otherwise be considered. Reduced systemic exposure may move biologically active compounds into use as drugs that would have been precluded due to their systemic toxicity.

Yet another advantage that can be conferred by conjugation and the subsequent change in pharmacokinetics of the therapeutic is the maintenance of steady state levels of drug diffusing off of the bone. This can improve the efficacy of not only bone localized target cells, such as bone infection, but can permit improvements to onerous dosing regimens and associated side effects. For example, oral antibiotics often cause gastrointestinal disturbances and such administration creates peaks and troughs in serum concentration levels (as is also seen with intravenous administration); this effect can be mitigated by steady state release of drug off of the bone.

One unanticipated benefit observed with the conjugate of etidronate to cytarabine is an expanded range of cancer cell types that can be targeted. Cytarabine is not used for epithelial solid tumors such as breast and prostate cancers due to its inability to penetrate the solid mass at a rate faster than the deaminating metabolism that causes its inactivation. Though not wishing to be bound by theory, it is believed the conjugation of cytarabine results in the slowing of the rate of the cytarabine inactivating metabolism such that the drug is now effective on breast and prostate cancer cells localized in the bone. In the case of the breast cancer model there was even a trend towards activity in primary mammary tumor.

Thus, the some of the advantages of the compounds and conjugates described herein can be summarized as follows:
1) Bone-targeted drug delivery;
2) Concentrations of drugs in the bone compartment not otherwise attainable;
3) Altered pharmacokinetics:
   a) more rapid systemic clearance, more rapid bone localization;
   b) reduced systemic exposure and thus reduced systemic toxicity;

c) steady state release from drug off the bone;
d) improved dosing regimens; and
4) Possible improvement in efficacy profile and pathogens targeted by a given drug.

The compounds of the present invention are effective over a wide dosage range and are generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

The present invention also encompasses the pharmaceutically-acceptable non-toxic acid addition salts of the compounds of the present invention and pharmaceutically acceptable formulations containing them. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The pharmaceutical compositions of the present invention are preferably formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient or excipients. The compositions can be formulated so as to provide sustained or delayed release of active ingredient after administration to the patient by employing procedures well known in the art.

Pharmaceutical compositions of the present invention comprise one or more bisphosphonate conjugates of the present invention associated with at least one pharmaceutically-acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

In preparing a pharmaceutical formulation of the present invention, it may be necessary to mill the active compound to provide the appropriate particle size prior to combining with the other ingredients. If the active compound is substantially insoluble, it is ordinarily milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

Synthesis of Bisphosphonate Conjugates

Novel bisphosphonate conjugates, i.e., molecules containing the phosphorus-oxygen-phosphorus-carbon-phosphorus backbone, are structurally similar to derivatives and analogs of nucleoside-5'-triphosphates or other polyphosphates. Those ordinarily skilled in the art recognize that known methods of monophosphorylation of OH and/or $NH_2$ (see for example Butorine et al, *Nucleosides, Nucleotides and Nucleic acids,* 2003, 22, 1267-72.) groups can be applied for the generation of phosphoryl derivative of the therapeutic agent having in its structure free hydroxyl or amino-group. Subsequent condensation with tri-n-butylammonium salts of bisphosphonic acids provides the conjugates described herein (FIGS. 2 and 3). It is also recognized that compounds of the invention can be made by direct condensation with therapeutic compound if the latter has free phosphate or phosphonate group in its structure, suitable for such condensation (FIG. 4). Known methods for synthesis of nucleoside-5'-triphosphates were tested to find effective experimental protocols for synthesis and purification of novel bisphosphonate conjugates. A variety of chemical methods for the preparation of nucleoside-5'-triphosphates from nucleoside monophosphates are known. Referring to FIG. 1, the nucleoside monophosphates were activated as imidazolides using the 1,1'-carbonyldiimidazole method because the reaction of mononucleotides with 1,1'-carbonyldiimidazole (CDI) occurs under relatively mild conditions compared with other methods and does not require a purification step.

Additional objects, advantages, and novel features of this invention will become apparent to those skilled in the art upon examination of the following examples thereof, which are not intended to be limiting.

EXAMPLES

Example 1

Synthesis of 5'-Fluoro-1-(2'-hydroxyethoxymethyl) uracil

The said compound was prepared according to M. Ya. Karpeisky et al, Khim. Heterocycl. Soedinenii (USSR) 1980, 11, 1541-1544.

Example 2

Synthesis of $N^4$-benzoyl-1-(2',3'-di-O-acetyl-β-D-arabinofuranosyl)cytosine

The compound was obtained analogously starting from $N^4$-benzoyl-β-D-arabinofuranosyl)cytosine (10 mmol) Yield 2.8 g (65%).
$^1$H NMR (400.13 MHz) (CDCl$_3$) δ: 8.31 d (1H, $J_{6,5}$=7.5 Hz, H-6); 7.93-7.48 m (5H, Bz), 7.67 d (1H, H-5); 6.37 d (1H, $J_{1',2'}$=4.3 Hz, H-1'), 5.63 dd (1H, $J_{2',3'}$=2.7 Hz, H-2'), 5.24 dd (1H, $J_{3',4'}$=4.1 Hz, H-3'), 4.12 ddd (1H, H-4'), 4.01 dd (1H, $J_{5'a,4'}$=3.6 Hz, $J_{5'a,5'b}$=12.3 Hz, H-5'a), 3.92 dd (1H, $J_{5'b,4'}$=4.7 Hz, H-5'b) 2.12 s (3H, Ac), 1.98 s (3H, Ac)

Example 3

Synthesis of 5-Fluorouridine 5'-monophosphate

The mixture of 2',3-di-O-acetyl-5-fluorouridine (5 mmol) and 10 ml 1M solution β-cyanoethyl phosphate in pyridine was evaporated in vacuo and dried by coevaporations with dry pyridine (2×10 ml). The residue was dissolved in 20 ml of the same solvent, N,N-dicyclohexylcarbodiimide (DCC, 40 mmol) was added and the mixture was stored at 200° C. for 4 days. After addition of water (15 ml) the precipitating dicyclohexyl urea was filtered off and washed with 50 ml of 20% aqueous pyridine. The combined filtrates were washed with ether (2×30 ml) and concentrated in vacuo to remove the traces of ether, and then applied to a column of DEAE-cellulose (200 ml, $HCO_3^-$ form). The column was washed with water (500 ml) and eluted with 0.05 M solution of $NH_4HCO_3$. Fractions absorbing in the UV were combined, evaporated in vacuo, coevaporated with water (5×10 ml). The residue was dissolved in 40 ml of 1N NaOH and kept 20 min at 20° C. The solution was applied onto a column of Dowex 50 ($H^+$-form) and eluted with water, the resulting solution of monophosphate was neutralized by addition of 2.5% ammonia and evaporated in vacuo. The residue was dissolved in 50 ml of water and applied to a column of DEAE-cellulose (200 ml, $HCO_3^-$ form). The column was washed with water (500 ml), 0.05 M of $NH_4HCO_3$ and eluted with 0.1 M solution of $NH_4HCO_3$. Fractions absorbing in the UV were combined, evaporated in vacuo, coevaporated with water (5×10 ml). The residue was dissolved in 40 ml of water and freeze dried. 5-Fluorouridine-5'-monophosphate was obtained as ammonium salt. Yield 2.4 mmol (48%).
$^1$H-NMR (400.13 MHz) (D$_2$O) δ: 8.16 d (1H, $J_{6,F}$ 6.5 Hz, H-6), 5.92 dd (1H, $J_{1',2'}$ 4.9 Hz, $J_{1',F}$=1.4 Hz, H-1') 4.32 t (1H, $J_{3',2'}$=5.0 Hz, $J_{3',4'}$=5.1 Hz, H-3'), 4.29 t (1H, H-2') 4.22 m (1H, H-4'), 4.06 ddd (1H; $J_{4'5'a-b}$=3.8 Hz, $J_{5'a,5'b}$=11.8 Hz, $J_{5'a-P}$=2.8 Hz, H-5'a), 3.98 ddd (1H, $J_{5'b,5'a}$=5.1 Hz, $J_{5'b-P}$=2.9 Hz, H-5'b).

Example 4

Synthesis of 5-Fluoro-1-(2'-hydroxyethoxymethyl)-uracil-2'-monophosphate

The mixture of 5-fluoro-1-(2'-hydroxyethoxymethyl)uracil (4.6 mmol) and 9.2 ml 1M solution of β-cyanoethyl phosphate in pyridine was evaporated in vacuo and dried by coevaporations with dry pyridine (2×10 ml). The residue was dissolved in 20 ml of the same solvent, DCC (37 mmol) was added and the mixture was stored at 20° C. for 4 days. After addition of water (15 ml), the precipitating dicyclohexyl urea was filtered off and washed with 50 ml of 20% aqueous pyridine. The combined filtrates were washed with ether (2×30 ml) and concentrated in vacuo to remove the traces of ether and then applied to a column of DEAE-cellulose (200 ml, $HCO_3^-$ form). The column was washed with water (500 ml) and eluted with 0.05 M solution of $NH_4HCO_3$. Fractions absorbing in the UV were combined, evaporated in vacuo, coevaporated with water (5×10 ml). The residue was dissolved in 40 ml of 1N NaOH and kept for 20 min at 20° C. The solution was applied onto a column of Dowex 50 ($H^+$ form) and eluted with water, the resulting solution of monophosphate was neutralized by addition of 2.5% ammonia, evaporated in vacuo. The residue was dissolved in 50 ml of water and applied to a column of DEAE-cellulose (200 ml, $HCO_3^-$-form). The column was washed with water (500 ml) 0.05 M of $NH_4HCO_3$ and eluted with 0.1 M solution of $NH_4HCO_3$. Fractions absorbing in the UV were combined, evaporated in vacuo, coevaporated with water (5×10 ml). The residue was dissolved in 40 ml of water and freeze dried. 5-Fluoro-1-(2'-hydroxyethoxymethyl)uracil-2'-monophosphate was obtained as ammonium salt. Yield 2.07 mmol (45%).
$^1$H-NMR (400.13 MHz) (D$_2$O) δ: 7.98 d (1H, $J_{6,F}$=5.7 Hz, H-6), 5.19 s (2H, CH$_2$N), 3.91 m (2H, CH$_2$), 3.75 m (2H, OCH$_2$)

Example 5

Synthesis of 1-(β-D-Arabinofuranosyl)cytosine-5'-monophosphate

The mixture of $N^4$-bensoyl-1-(2',3'-di-O-acetyl-β-D-arabinofuranosyl)cytosine (2 mmol) and 4 ml 1M solution of β-cyanoethyl phosphate in pyridine was evaporated in vacuo and dried by coevaporations with dry pyridine (2×10 ml). The residue was dissolved in 5 ml of the same solvent, DCC (16 mmol) was added and the mixture was stored at 20° C. for 4 days. After addition of water (15 ml), the precipitating dicyclohexyl urea was filtered off and washed with 50 ml of 20% aqueous pyridine. The combined filtrates were washed with ether (2×20 ml) and concentrated in vacuo to remove the traces of ether, and then applied to a column of DEAE cellulose (200 ml, HCO$_3$ form). The column was washed with water (500 ml) and eluted with 0.05M solution of $NH_4HCO_3$. Fractions absorbing in the UV were combined, evaporated in vacuo, coevaporated with water (5×10 ml). The residue was dissolved in 25 ml of 1N NaOH and kept for 20 min. at 20° C. The solution was applied onto a column of Dowex-50 ($H^+$ form) (40 ml) and eluted with mixture pyridine-water 1:4 (100 ml), the resulting solution evaporated in vacuo, coevaporated with water (2×10 ml) and methanol (2×20 ml). The residue was dissolved in 5 ml 5M NH$_3$ in methanol and kept at 20° C. for 4 days. The reaction mixture was dissolved in 50 ml of water, washed with chloroform (2×20 ml) and concentrated in vacuo to remove the traces of chloroform and then applied to a column of DEAE-cellulose (200 ml, HCO$_3^-$ form). The column was washed with water (500 ml), 0.05 M NH4HCO3 and eluted with 0.1 M NH$_4$HCO$_3$. Fractions absorbing in the UV were combined, evaporated in vacuo, coevaporated with water (5×10 ml). The residue was dissolved in 40 ml of water and freeze dried. Yield 0.82 mmol (41%).

$^1$H NMR (400.13 MHz) (D$_2$O) δ: 7.93 d (1H, J$_{6,5}$=7.7 Hz, H-6), 6.22 d (IH', J$_{1',2'}$=5.3 Hz, H-1'), 6.08 d (1H, H-5), 4.43 t (1H, J$_{2',3'}$=51 Hz, H-2), 4.20 t (1H, J$_{3',4'}$=5.2 Hz, H-3'), 4.15 m (1H, H-4'), 4.09 m (2H, H-5'a, 5'b)

Example 6

Synthesis of Bisphosphonate—Nucleotide Conjugates

General

NMR spectra were recorded on a Bruker AMX 400 spectrometer at 300K in D$_2$O. The chemical shifts were related to the water signal at 4.6 ppm. The signals were assigned by the aid of phosphorus decoupling measurements. The TLC-chromatography was performed on Kieselgel 60 F$_{254}$ plates developed in 2-propanol/NH$_3$ (aq., conc.)/water 7:1:2 (system A); water/NH$_3$ (aq., conc.)/trichloracetic acid/methanol 6:3:1:10 (system B) or on PEI-cellulose plates in 0.25 M NH$_4$HCO$_3$ (system C); 1M LiCl (system D); 0.15 M KH$_2$PO$_4$ (system E); 0.5 M NH$_4$HCO$_3$ (system F). HPLC-analysis: Column Nucleosil C-18 (30-C18), 0-4% triethylammonium acetate (0.1M, pH6.8); 20 min, flow rate 1 ml/min.

Conjugate Synthesis

To the solution of 0.2 mmol nucleotide tri-nbutylammonium salt in DMF (3 ml) 1,1'carbonyldumidazole (98 mg, 0.6 mmol) was added. The reaction mixture was stirred 1 h at room temperature, then 0.8 ml of 1M solution of methanol in DMF was added, followed after 20 min. by a solution of tri-n-butylammonium salt of diphosphonic acid (1 mmol) in DMF. The reaction mixture was stirred at room temperature 16 hours, the crystalline material formed was filtered off, washed with DMF, and the solution was evaporated in vacuo to dryness.

Isolation and Purification

Method A (Compounds I-III, FIG. 1)

The residue after evaporating to dryness was dissolved in 20 ml water and purified on DEAE-cellulose (HCO$_3^-$). The column was washed with water (500 ml) and then eluted with a linear gradient NH$_4$HCO$_3$ (0.05M-0.3M). Conjugates were eluted in 0.21 M NH$_4$HCO$_3$. The peak eluate was evaporated, the residue coevaporated with water. Lyophilization of the aqueous solution afforded ammonium salt of conjugates.

Method B (Compounds IV-IX, FIG. 1)

After evaporating, the residue was dissolved in 20 ml 0.02 M AcOLi in 0.02 M AcOH and purified on DEAE-cellulose (AcO$^-$ form). The column was washed with 0.02M AcOLi in 0.02M AcOH (200 ml), 0.04M AcOLi in 0.04M AcOH (300 ml). Analog of triphosphate was eluted in 0.2M AcOLi in 0.2M AcOH. The peak eluate was evaporated, the residue was centrifuged with ethanol (4×100 ml), dissolved in water. Lyophilisation of the water solution afforded Li salt of a triphosphate analog.

In the case of the analogs (VI) and (VII) residue after lyophilisation was dissolved in 20 ml 0.5% solution triethylamine in water, the solution was kept at room temperature 30 min and lyophilized. Residue was dissolved in 2 ml water and applied to a Dowex-50 (Na$^+$) column. Sodium salt of triphosphate analogs were eluted with water and lyophilized.

TABLE A

Conjugates obtained

Anhydride of 1-(2'-hydroxyethoxymethyl)-5-fluorouracil-2'-phosphate and methylenediphosphonic acid, NH$_4$-salt, method A, (II, FIG. 1)

Yield 58 mg, 55%.
R$_f$ 0.05 (A); R$_f$ 0.1(C); R$_f$ 0.32 (D); R$_f$ 0.34 (E).
$^1$H NMR (D$_2$O) δ: 7.89 d (1H, J $_{6H, F}$ = 5.5; 6-H); 5.25 s (2H, N—CH$_2$); 4.0 m (2H, CH$_2$); 3.78 m (2H, CH$_2$); 2.22 t (2H, J = 20.0; P—CH$_2$—P).
$^{31}$P NMR (D$_2$O) δ: −10.0 (1P, Jp$_\alpha$, p$_\beta$ = _23.0; Pα); 11.8 m (1P, Pβ; 14.2 m (1P, Pγ).
Anhydride of inosine-5'-monodihosphoric acid and 1-hydroxyethylidene-1,1-disphosphonic acid, Li-salt, method B, (IV, FIG. 1).

Yield 95 mg, 84%.
R$_f$ 0.04 (B); R$_f$ 0.05 (C); R$_f$ 0.3 (D); R$_f$ 0.16(E). HPLC: 99.5%; RT 8.98 min. (Li-salt).
$^1$H NMR (D$_2$O) δ: 8.47 s (1H, 8-H); 8.2 s (1H, 2-H); 6.2 br.s (1H, 1'-H); 4.6 m (2H, 2', 3'-H); 4.41 m (1H, 4'-H); 4.28 m(2H, 5'-CH$_2$); 1.56 t (3H, J = 12, 0; CH$_3$).
$^{31}$P NMR (D$_2$O) δ: −9.3 m(1P, Pα); 17.0 m (1P, Pβ); 17.2 m (1P, Pγ).
Anhydride of I-(2'-hydroxvethoxymethyl)-5-fluorouracil-2'-phosphate and 1-hydroxyethylidene-1,1-disphosphonic acid, Li-salt, method B, (V, FIG. 1)

Yield 60 mg, 61%.
R$_f$ 0.05(B); R$_f$ 09 (C); R$_f$ 0.32 (D). HPLC: 96.6%; RT 5.88 min. Na-salt.
$^1$H NMR(D$_2$O) δ: : 7.72 d (1H, J$_{H, F}$ = 5.5, 6-H); 5.18 s (2H, N—CH$_2$); 4.09 t (2H, CH$_2$); 3.79 t (2H, CH$_2$); 1.5 t (3H, J$_{H, P}$ = 15; CH$_3$).
$^{31}$P NMR (D$_2$O) δ: −8.8 d (1P, J$_{P\alpha P\beta}$ _ 33.3; Pα); 16.2 dd (1P, Pβ); 16.8 d (1P, J$_{P\beta P\gamma}$ _ 33.0; Pγ)
Anhydride of 5-fluorouridine-5'-monophosphoric acid and 1-hydroxyethvlidene-1~I-disphosphonic acid Na-salt, method B, (VI, FIG. 1).

Yield 78 mg, 65%.
R$_f$ 0.21 (C); R$_f$ 0.2 (D); R$_f$ 0.31 (E). HPLC: 96.6%; RT 6.18 min. Na-salt).
$^1$H NMR (D$_2$O) δ: 7.88 d (1H, J$_{H, F}$ = 6.2; 6-H); 5.97 d (1H, J$_{1', 2'}$ _ 4.5; 1'-H); 3.38 m (1H, 2'-H); 4.3 m (1H, 3'-H); 4.24 m (3H, 4'-H, 5'-CH$_2$); 1.54 t (3H, J$_{H, P}$ = 14.9; CH$_3$).

TABLE A-continued

Conjugates obtained $^{31}$P NMR (D$_2$O) δ: −9.2 d (1P, J$_{P\alpha P\beta}$ = 30.0; Pα); 16.4 m (2P, Pβ, Pγ).
Anhydride of uridine-5'-monophosphoric acid and 1-hydroxyethylidene- 1,1 disphosphonic acid, Li-salt, method B (VII, FIG. 1).

Yield 80 mg, 75%.
R$_f$ 0.1 (C); R$_f$ 0.12 (D); R$_f$ 0.04 (E). HPLC: 97.3%; RT 3.49 min., Na-salt.
$^1$H NMR (D$_2$O) δ: 7.8 d (1H, J$_{6,5}$ 7.8; 6-H); 5.9 d (1H, J$_{1',2'}$ _ 3.8; 1'-H); 5.8 dd (1H, J$_{5,6}$ = 7.8; 5-H); 4.3 m (1H, 2'-H); 4.2 m (1H, 3'H); 4.19 m (3H, 4'-H, 5'-CH$_2$); 1.45 t (3H, J$_{P,H}$ = 15.0; CH$_3$).
$^{31}$P NMR (D$_2$O, pH 9.3) δ: −9.2 d (1P, J$_{P\alpha P\beta}$ _ 32.0; Pα ); 16.2 m (2P, Pβ, Pγ);
(D$_2$O pH 5.3) δ: −9.2d (1P, J$_{P\alpha P\beta}$ _ 31.7; Pα); 2.8 dd (1P, J$_{P\beta, P\gamma}$ _ 33.7, Pβ;) 17.8 d (1P, J$_{P\gamma, P\beta}$ = 33.7; P$_\gamma$)

Example 7

Synthesis of anhydride of Inosine-5'-monophosphoric acid and Methylenedisphosphonic acid, NH$_4^+$ salt, (I, FIG. 1)

Tri-n-butylammonium salt in dry DMF (3 ml) and 1,1'-carbonyldiimidazole (98 mg, 0.6 mmol) was added to a solution of 0.2 mmol of Inosine-5'-monophosphate. The reaction mixture was stirred 1 h at room temperature. TLC analysis in system iso-PrOH—NH$_4$OH—H$_2$O (7:1:2) showed that mononucleotide was completely converted to a corresponding imidazolide (R$_f$ 0.1–>0.6). The 0.8 ml of 1M solution of methanol in dry DMF was added, after 20 mm solution of tri-n-butylammonium salt of methylenediphosphonic acid (1 mmol) in DMF (3 ml) was added. The reaction mixture was stirred 16 h at room temperature. The crystalline material was filtered off, washed with DMF and the solution was evaporated in vacuo to dryness. The residue, after evaporating, was dissolved in 20 ml water and was applied to a column of DEAE-cellulose (100 ml, HCO$_3^-$ form). The column was washed with water (500 ml) and then eluted with a linear gradient of NH$_4$HCO$_3$ (0.05–>0.3 M). The triphosphate analog was eluted in 0.21 M NH$_4$HCO$_3$. The peak eluate was evaporated and the residue was coevaporated with water (5×10 ml). Lyophilization of the water solution afforded ammonium salt of triphosphate analog. Yield 85 mg, 74%. R$_f$ 0.05 (A); 0.04 (B); 0.25 (C); 0.16 (D). HPLC (Column Nucleosil C-18 (30-C18), 0-4% triethylammonium acetate (0.1M, pH 6.8), 20 min., flow rate 1 ml/min): 100%, RT 7.2 min, Na salt)
$^1$H NMR (D$_2$O) δ: 8.45 s (1H, 8-H); 8.2 s (1H, 2-H); 6.1 d (1H, J$_{1',2'}$=5.4; 1'-H); 4.55 m (1H, 3'-H); 4.39 m (1H, 4'-H); 4.25 m (2H, 5'-CH$_2$); 2.32 t (2H, J$_{H,P}$=20; P—CH$_2$—P).
$^{31}$P NMR (D$_2$O) δ: −10.2 d (1P, J$_{P\alpha P\beta}$=25; Pα); 9.8br d (1P, Pβ); 15.4 d (1P, J$_{P\beta,P\gamma}$=7.0; Pγ)

Example 8

Synthesis of anhydride of 1-(2'-hydroxyethoxymethylene)-5-Fluorouracil-2'-phosphoric acid and 1-hydroxyethyliden-1,1-diphosphonic acid, Li salt (V, FIG. 1)

To the solution of 0.2 mmol 1-(2-hydroxyethoxymethylene)-5-Fluorouracyl-2'-phosphonic acid tri-n-butylammonium salt in dry DMF (3 ml) 1,1'-carbonyldiimidazole (98 mg, 0.6 mmol) was added. The reaction mixture was stirred for 1 hour at room temperature. TLC analysis in system iso-PrOH—NH$_4$OH—H$_2$O (7:1:2) showed that mononucleotide was completely converted to a imidazolide (R$_f$ 0.15–>0.65). Then 0.8 ml 1M solution methanol in dry DMF was added, after 20 mm solution of tri-n-butylammonium salt of 1-hydroxyethylidene-1,1-disphosphonic acid (1 mmol) in DMF (3 ml) was added. The reaction mixture was stirred 16 h at room temperature. The crystalline material was filtered off and washed with DMF. The solution was evaporated in vacuo to dryness. The residue, after evaporating, was dissolved in 20 ml 0.02M AcOLi in 0.02M AcOH and was applied on to column of DEAE-cellulose (100 ml, AcO$^-$ form). The column was washed with 0.02 N AcOLi in 0.02M AcOH (200 ml), 0.04M AcOLi in 0.04M AcOH (300 ml). The triphosphate analog was eluted in 0.2M AcOLi in 0.2M AcOH. The peak eluate was evaporated; the residue was centrifuged with ethanol (4×100 ml) and then dissolved in water. Lyophilization of the water solution afforded Li salt of triphosphate analog. Yield 60 mg, 61%. R$_f$: 0.05 (B); 0.09 (C); 0.32 (1).
HPLC (Column Nucleosil C-18 (30-C 18), 0-4% triethyl ammonium acetate (0.1 M, pH 6.8), 20 mm, flow rate 1 ml/min): 96.6%, RT 5.88 min (Na salt)
$^1$H NMR (D$_2$O) δ: 7.72 d (J$_{H-F}$=5.5; 6H); 5.18 s (2H, N-5-CH$_2$); 3.79 t (2H, CH$_2$); 1.5 t (3H, J$_{H,P}$=15; CH$_3$)
$^{31}$P NMR (D$_2$O) δ: −8.8 d (1P, J$_{P\alpha P\beta}$=33.3; Pα;); 16.2 dd (1P, 1P, J$_{P\beta,P\gamma}$=7.0; Pγ)

Example 9

Synthesis of anhydride of 5-Fluoro-uridine-5'-monophosphoric acid and 1-Hydroxyethylidene-1,1-diphosphonic acid, Sodium salt (VI, FIG. 1)

To the solution of 0.2 mmol 5-Fluoro-uridine-5'-monophosphate tri-n-butylammonium salt in dry DMF (3 ml) 1,1-carbonyldiimidazole (98 mg, 0.6 mmol) was added. The reaction mixture was stirred 1 h at room temperature. TLC analysis in system iso-PrOH—NH$_4$OH—H$_2$O (7:1:2) showed that mononucleotide was completely converted to a imidazolide (R$_f$ 0.13–>0.7). Then 0.8 ml 1M solution methanol in dry DMF was added, after 20 min solution of tri-n-butylammonium salt of 1-hydroxyethylidene-1,1-diphosphonic acid (1 mmol) in DMF (3 ml) was added. Reaction mixture was stirred 16 h at room temperature. The crystalline material was filtered off, washed with DMF, and the solution was evaporated in vacuo to dryness. The residue, after evaporating, was dissolved in 20 ml 0.02M AcOli in 0.02M AcOH and was applied on to column of DEAE-cellulose (100 ml, AcO$^-$ form). The column was washed with 0.02 M AcOLi in 0.02 M AcOH (200 ml), 0.04 M AcOLi in 0.04 M AcOH (300 ml). The triphosphate analog was eluted in 0.2 M AcOLi in 0.2M AcOH. The peak eluate was evaporated, the residue was centrifuged with ethanol (4×100 ml), dissolved in 15 ml water and freeze dried. The residue was dissolved in 20 ml of 0.5% solution of triethylamine in water and kept for 30 min. at 20° C. and freeze dried. The residue was dissolved in 2 ml water and was applied on to a column of Dowex-50 (1 ml, Natform). Na salt of triphosphate analog was eluted with water and freeze dried. Yield 78 mg, 65%. $R_f$: 0.05 (B); 0.21 (C); 0.2 (D); 0.31 (E).

HPLC (Column Nucleosil C-18 (30-C18), 0-4% triethyl-ammonium acetate (0.1M, pH 6.8), 20 min., flow rate 1 ml/min): 96.6%, RT 6.18 min (Na salt)

$^1$H NMR (D$_2$O) δ: 7.88 d (1H, $J_{H,F}$=6.2; 6-H); 5.97 d (1H, $J_{1',2'}$=4.5; 1'-H); 3.38 m (1H, 2'-H); 4.3 m (1H, 3'-H); 4.24 m (3H, 4'-H, 5'-CH$_2$); 1.54 t (3H, $J_{H,P}$=14.9; CH$_3$).

$^{31}$P NMR (D$_2$O) δ: −9.2 d (1P, $J_{P\alpha,P\beta}$=30.0; $P_\alpha$); 16.4 m (2P, $P_{\beta_-}$, $P_\gamma$).

Example 10

Ex Vivo Stability of Bisphosphonate Conjugates in Mouse and Human Serum

The hydrolysis reactions were carried out in sealed tubes immersed in a thermostated water bath (37.0±0.1° C.). HPLC analysis of the decomposition of starting conjugates was followed by HPLC using Atlantis C18 column (4.6×250 mm, 5 μm) using 0.1 mol L$^{-1}$ KH$_2$PO$_4$ with 2 mM EDTA as an eluent. The half-lives observed are summarized in Table 1.

TABLE 1

Half-lives for the hydrolysis of conjugates to corresponding monophosphates in mouse and human serum at 37° C.

| Compound | Human serum $T_{1/2}$, h | Mouse serum $T_{1/2}$, h |
|---|---|---|
| VI | 3.5 | 17.4 |
| III | 2.9 | 0.4 |
| VIII | 5.7 | 33 |

Example 11

Binding of Bisphosphonate Conjugates (BC) on Hydroxyapatite Powder

A. To estimate the binding of BC on hydroxyapatite (mineral component of a bone) UV spectra of BC in buffer pH 7 were recorded before and after treatment with hydroxyapatite. To this end 10 μl of hydroxyapatite suspension in water was added to 1 ml of ~10$^{-4}$ M solution of a BC in 0.1 M Tris-HCl buffer, pH 7.0, 0.15 M NaCl and the mixture was intensively shaken for 10 minutes, and centrifuged for 5 minutes at 10,000 rpm in a microcentrifuge. The supernatant was separated and an absorbency spectrum of the supernatant was recorded. The corresponding values of peaks absorbency before and after hydroxyapatite treatment are given in Table 2.

B. The mineral-binding ability of various BC compounds has been also elucidated by comparing their retention times during HPLC on a hydroxyapatite column (Bio-Scale CHT10-1, 12 mm×88 mm); 1.5 mol L$^{-1}$ potassium phosphate buffers (pH 5.8, 6.8, and 7.8) and 0.5 mol L$^{-1}$ sodium phosphate (pH 6.8) were used as eluents. The flow rate was 2 mL min$^{-1}$. Compounds III, VI and VIII were detected by UV absorbance at 270 nm. Nucleoside mono-, di-, and triphosphates were recorded at a wavelength of 260 nm and zoledronate at a wavelength of 218 nm. The concentration of the eluted compounds was 0.3 mmol L$^{-1}$.

TABLE 3

Retention times of compounds on hydroxyapatite column Bio-Scale CHT10-I, 12 mm × 88 mm (sodium phosphate buffer, pH = 6.8, 2 mL/min)

| Compound | 1500 mM sodium phosphate buffer (retention time in min) | 500 mM sodium phosphate buffer (retention time in min) |
|---|---|---|
| Zoledronate | 17.35 | |
| VI | 6.00 | 17.72 |
| VIII | 5.92 | 20.29 |
| III | 3.82 | 6.08 |
| UMP | 3.42 | 4.25 |
| UDP | 3.47 | 5.75 |
| UTP | 3.5 | |

The data obtained (Table 3) clearly shows that the etidronate analogs (VI and VIII) exhibit to hydroxyapatite higher affinity than UTP and the medronate analogs (III), but lower affinity than zoledronate. The identity of the base moiety and the configuration of the sugar moiety do not appear to play a significant role in binding.

Example 12

In Vivo Bone Distribution

Sprague-Dawley Crl:CD(SD)BR rats in groups of three were intravenously injected with ~1 mg/kg of [$^{14}$C] radio-labeled araC-etidronate conjugate (VIII, FIG. 1) or aracytidine (equimolar radiolabel at the C2 position of the nucleoside) and bone associated radioactivity was measured 30, 60 and 300 minutes post dosing. The resulting distribution to femur is shown in FIG. 6. Greater than a two-fold improvement was observed in the amount of Ara-C on bone when conjugated to the bisphosphonate. Furthermore, a decrease in the radioactivity over the 5-hour time course of the experiment was found. This observation is consistent with a rapid binding to bone followed by release of the cytotoxic nucleoside occurring on the time scale desired for improved drug delivery to the bone target. The data above is evidence that the current invention is able to increase the concentra-

TABLE 2

UV-spectra of novel bisphosphonate conjugates

| Compound | Peak wavelength, nm | Before hydroxyapatite addition | After hydroxyapatite addition | % of nonbound compound | % of bound compound |
|---|---|---|---|---|---|
| I | 249 | 1.158 | 0.086 | 7.43 | 92.57 |
| II | 266 | 0.667 | 0.085 | 12.74 | 87.26 |
| III | 269 | 0.778 | 0.233 | 29.95 | 70.05 |
| VI | 269 | 0.567 | 0.172 | 30.34 | 69.66 |
| VIII | 272 | 0.795 | 0.09 | 11.32 | 88.68 | tion of a therapeutic payload to the bone beyond the level that can be achieved by current methods.

The foregoing discussion has been presented for purposes of illustration and description. The foregoing is not intended to limit the invention to the form or forms disclosed herein. Although the description has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bisphosphonate conjugate having the structure:

$$Y(L-A)_n$$

or a pharmaceutically acceptable acid addition salt thereof wherein:

n=1-3;

A is a bisphosphonate residue having the structure

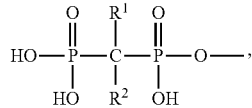

wherein $R^1$ is selected from the group consisting of OH, SH, $NH_2$, OZ, SZ, NZ, halogen, and H;

$R^2$ is selected from the group consisting of H, Z, and halogen;

Z is selected from the group consisting of alkyl, cycloalkyl, aryl, heteroaryl, and $NH_2$;

L is a linker having the structure:

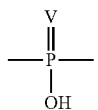

where V is O or S; and

Y is a residue of an anti-infective compound in a class selected from the group consisting of fluoroquinolones, lincosamides, oxazolidinones, aminoglycosides, cephalosporins, and glycopeptides.

2. A pharmaceutical composition comprising a conjugate of claim 1 and a pharmaceutically-acceptable carrier.

3. A method of treating bone infection, the method comprising administering a therapeutically effective amount of a conjugate of claim 1 or a pharmaceutical composition of claim 2 to a subject in need thereof.

4. A method of delivering an anti-infective compound to the bone or surrounding tissue, wherein the anti-infective compound is in a class selected from the group consisting of fluoroquinolones, lincosamides, oxazolidinones, aminoglycosides, cephalosporins, and glycopeptides, the method comprising administering a conjugate of claim 1 or a pharmaceutical composition of claim 2.

5. A method of treating inflammation caused by bone infection, the method comprising administering a therapeutically effective amount of a conjugate of claim 1 or a pharmaceutical composition of claim 2 to a subject in need thereof.

6. The conjugate of claim 1, wherein the anti-infective compound is a fluoroquinolone.

7. The conjugate of claim 1, wherein the anti-infective compound is a lincosamide.

8. The conjugate of claim 1, wherein the anti-infective compound is a oxazolidinone.

9. The conjugate of claim 1, wherein the anti-infective compound is an aminoglycoside.

10. The conjugate of claim 1, wherein the anti-infective compound is a cephalosporin.

11. The conjugate of claim 1, wherein the anti-infective compound is a glycopeptide.

* * * * *